(12) United States Patent
Saito et al.

(10) Patent No.: US 6,740,515 B1
(45) Date of Patent: May 25, 2004

(54) RECOMBINANT ADENOVIRUS

(75) Inventors: Izumu Saito, Tokyo (JP); Yumi Saito, Tokyo (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/856,110

(22) PCT Filed: Sep. 9, 1999

(86) PCT No.: PCT/JP99/04902

§ 371 (c)(1),
(2), (4) Date: Aug. 16, 2001

(87) PCT Pub. No.: WO00/29598

PCT Pub. Date: May 25, 2000

(30) Foreign Application Priority Data

Nov. 18, 1998 (JP) .......................................... 10-328566

(51) Int. Cl.⁷ .............................................. C12N 15/00
(52) U.S. Cl. ................ 435/235.1; 435/69.1; 424/199.1; 424/233.1
(58) Field of Search ........................ 435/235.1, 320.1; 536/23.72; 424/204.1, 233.1

(56) References Cited

FOREIGN PATENT DOCUMENTS

| EP | 0 732 405 A1 | 9/1996 |
|---|---|---|
| JP | 10-33175 | 2/1998 |
| JP | 11-196880 | 7/1999 |
| WO | WO 91/02801 | 3/1991 |

OTHER PUBLICATIONS

H. Van Ormondt, et al., "The Nucleotide Sequence of the Transforming HpaI–E Fragment of Adenovirus Type 5 DNA," Gene, 1978, 4, 309–328.

Hardy et al., "Construction of Adenovirus Vectors through Cre–lox Recombination", *Journal of Virology*, vol. 71, No. 3, Mar. 1997, pp. 1842–1849.

Parks et al., "A helper–dependent adenovirus vector system: Removal of helper virsu by Cre–mediated excision of the viral packaging signal", *Proc. Nat'l. Acad. Sci. USA*, vol. 93, Nov. 1996, pp. 13565–13570.

*Primary Examiner*—Laurie Scheiner
(74) *Attorney, Agent, or Firm*—Sughrue Mion, PLLC

(57) ABSTRACT

Recombinant adenoviruses comprising the following sequences in the genome: (1) a left inverted terminal repeat: (2) a packaging signal: (3) a recombinase recognition sequence located at a region in between said left inverted terminal repeat and said packaging signal: and (4) at least one more recombinase recognition sequence which is located downstream of said packaging signal and which is recognized by the recombinase that recognizes the above recombinase recognition sequence are useful as a material for constructing highly safe vectors for gene therapy in the field of gene therapy.

5 Claims, 4 Drawing Sheets

FIG. 2

INSERTION SITE OF THE loxP SEQUENCE ADJACENT TO THE PACKAGING SIGNAL

```
     Ad5   LEFT END    ITR
  1  CATCATCAAT AATATACCTT ATTTTGGATT GAAGCCAATA TGATAATGAG
 51  GGGGTGGAGT TTGTGACGTG GCGCGGGCG TGGGAACGGG GCGGGTGACG
                                                   AflIII
101  TAGTAGTGTG GCGGAAGTGT GATGTTGCAA GTGTGGCGGA ACACATGTAA
                                                        15L
        XhoI          loxP             MluI      KpnI
       GctcgagATAACTTCGTATAATGTATGCTATACGAAGTTATacgcgtTCGCTCggtaccCGCCATG
      GTActcgagATAACTTCGTATAATGTATGCTATACGAAGTTATacgcgtTCGCTCggtaccCGGCCGG
                                                                       19L
151  GCGACGGATG TGGCAAAAGT GACGTTTTTG GTGTGCGCCG GTGTACACAG
     PACKAGING SIGNAL                              SgrAI
201  GAAGTGACAA TTTTCGCGCG GTTTTAGGCG GATGTTGTAG TAAATTTGGG
251  CGTAACCGAG TAAGATTTGG CCATTTTCGC GGGAAAACTG AATAAGAGGA
301  AGTGAAATCT GAATAATTTT GTGTTACTCA TAGCGCGTAA TATTTGTCTA
351  GGGCCGCGGG GACTTTGACC GTTTACGTGG AGACTCGCCC AGGTGTTTTT
401  CTCAGGTGTT TTCCGCGTTC CGGGTCAAAG TTGGCGTTTT ATTATTATAG
451  TCAGC
```

FIG. 3

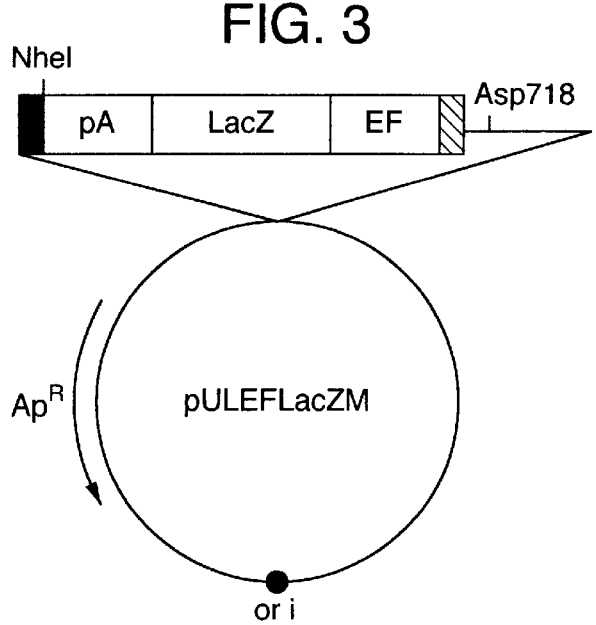

AxLEFLacZ15L OR AxLEFLacZ19L

SEQUENCE LISTING

<160> NUMBER OF SEQ ID NOS: 10

<210> SEQ ID NO 1
<211> LENGTH: 34
<212> TYPE: DNA
<213> ORGANISM: Bacteriophage P1

<400> SEQUENCE: 1
ataacttcgt ataatgtatg ctatacgaag ttat                                34

<210> SEQ ID NO 2
<211> LENGTH: 34
<212> TYPE: DNA
<213> ORGANISM: Bacteriophage P1

<400> SEQUENCE: 2
ataacttcgt atagcataca ttatacgaag ttat                                34

<210> SEQ ID NO 3
<211> LENGTH: 66
<212> TYPE: DNA
<213> ORGANISM: Artificial Sequence
<220> FEATURE:
<223> OTHER INFORMATION: Synthesized DNA sequence containing lox P
      sequence

<400> SEQUENCE: 3
gctcgagata acttcgtata atgtatgcta tacgaagtta tacgcgttcg ctcggtaccc    60
gccatg                                                               66

<210> SEQ ID NO 4
<211> LENGTH: 521
<212> TYPE: DNA
<213> ORGANISM: Artificial Sequence
<220> FEATURE:
<223> OTHER INFORMATION: 5'-terminus seq. of adenovirus 5-type genome in
      plasmid pycw15L

<400> SEQUENCE: 4
catcatcaat aatatacctt attttggatt gaagccaata tgataatgag ggggtggagt    60
ttgtgacgtg gcgcggggcg tgggaacggg gcgggtgacg tagtagtgtg gcggaagtgt   120
gatgttgcaa gtgtggcgga acacatggct cgagataact tcgtataatg tatgctatac   180
gaagttatac gcgttcgctc ggtacccgcc atgtaagcga cggatgtggc aaaagtgacg   240
tttttggtgt gcgccggtgt acacaggaag tgacaatttt cgcgcggttt taggcggatg   300
ttgtagtaaa tttgggcgta accgagtaag atttggccat tttcgcggga aaactgaata   360
agaggaagtg aaatctgaat aattttgtgt tactcatagc gcgtaatatt tgtctagggc   420
cgcggggact tgaccgtttt acgtggagac tcgcccaggt gtttttctca ggtgttttcc   480
gcgttccggg tcaaagttgg cgttttatta ttatagtcag c                       521

<210> SEQ ID NO 5
<211> LENGTH: 60
<212> TYPE: DNA
<213> ORGANISM: Artificial Sequence
<220> FEATURE:
<223> OTHER INFORMATION: Synthesized DNA sequence containing mutated lox
      P sequence

<400> SEQUENCE: 5
tcgagtccgg aataacttcg tataacgtat actatacgaa gttatgctag catttaaatg    60

<210> SEQ ID NO 6
<211> LENGTH: 60
<212> TYPE: DNA
<213> ORGANISM: Artificial Sequence
<220> FEATURE:
<223> OTHER INFORMATION: Synthesized DNA sequence containing mutated lox
      P sequence

<400> SEQUENCE: 6
tcgacattta aatgctagca taacttcgta tagtatacgt tatacgaagt tattccggac    60

<210> SEQ ID NO 7
<211> LENGTH: 68
<212> TYPE: DNA
<213> ORGANISM: Artificial Sequence
<220> FEATURE:
<223> OTHER INFORMATION: Synthesized DNA sequence containing lox P
      sequence

<400> SEQUENCE: 7
gtactcgaga taacttcgta taatgtatgc tatacgaagt tatacgcgtt cgctcggtac    60
ccggccgg                                                             68

<210> SEQ ID NO 8
<211> LENGTH: 523
<212> TYPE: DNA
<213> ORGANISM: Artificial Sequence
<220> FEATURE:
<223> OTHER INFORMATION: 5'-terminus seq. of adenovirus 5-type genome in
      plasmid pycw19L

<400> SEQUENCE: 8
catcatcaat aatataccti attttggatt gaagccaata tgataatgag ggggtggagt    60
ttgtgacgtg gcgcggggcg tgggaacggg gcgggtgacg tagtagtgtg gcggaagtgt   120
gatgttgcaa gtgtggcgga acacatgtaa gcgacggatg tggcaaaagt gacgtttttg   180
gtgtgcgccg ggtactcgag ataacttcgt ataatgtatg ctatacgaag ttatacgcgt   240
tcgctcggta cccggccggt gtacacagga agtgacaatt ttcgcgcggt tttaggcgga   300
tgttgtagta aatttgggcg taaccgagta agatttggcc attttcgcgg gaaaactgaa   360
taagaggaag tgaaatctga ataattttgt gttactcata gcgcgtaata tttgtctagg   420
gccgcgggga ctttgaccgt ttacgtggag actcgcccag gtgtttttct caggtgtttt   480
ccgcgttccg ggtcaaagtt ggcgttttat tattatagtc agc                     523

<210> SEQ ID NO 9
<211> LENGTH: 455
<212> TYPE: DNA
<213> ORGANISM: Human Adenovirus 5

<400> SEQUENCE: 9
catcatcaat aatataccti attttggatt gaagccaata tgataatgag ggggtggagt    60
ttgtgacgtg gcgcggggcg tgggaacggg gcgggtgacg tagtagtgtg gcggaagtgt   120
gatgttgcaa gtgtggcgga acacatgtaa gcgacggatg tggcaaaagt gacgtttttg   180
gtgtgcgccg gtgtacacag gaagtgacaa ttttcgcgcg gttttaggcg gatgttgtag   240
taaatttggg cgtaaccgag taagatttgg ccatttttcgc gggaaaactg aataagagga   300
agtgaaatct gaataatttt gtgttactca tagcgcgtaa tatttgtcta ggccgcgggg   360

-continued

```
gactttgacc gtttacgtgg agactcgccc aggtgttttt ctcaggtgtt ttccgcgttc    420
cgggtcaaag ttggcgtttt attattatag tcagc                              455

<210> SEQ ID NO 10
<211> LENGTH: 454
<212> TYPE: DNA
<213> ORGANISM: Human Adenovirus 2

<400> SEQUENCE: 10
catcatcata atataccttta ttttggattg aagccaatat gataatgagg gggtggagtt   60
tgtgacgtgg cgcgggggcgt gggaacgggg cgggtgacgt agtagtgtgg cggaagtgtg   120
atgttgcaag tgtggcggaa cacatgtaag cgccggatgt ggtaaaagtg acgtttttgg   180
tgtgcgccgg tgtatacggg aagtgacaat tttcgcgcgg ttttaggcgg atgttgtagt   240
aaatttgggc gtaaccaagt aatgtttggc cattttcgcg ggaaaactga ataagaggaa    300
gtgaaatctg aataattctg tgttactcat agcgcgtaat atttgtctag ggccgcgggg   360
actttgaccg tttacgtgga gactcgccca ggtgttttc tcaggtgttt tccgcgttcc    420
gggtcaaagt tggcgtttta ttattatagt cagc                               454
```

RECOMBINANT ADENOVIRUS

TECHNICAL FIELD

The present invention relates to recombinant adenovirus that becomes a material for constructing highly safe vectors for gene therapy in the field of gene therapy.

BACKGROUND ART

Adenovirus is considered to be a promising vector for use in gene therapy because of its high efficiency of gene transfer, its ease of preparing high titer viral solutions, its ability of introducing genes into non-growing cells. Adenovirus vectors in common use now are replication-defective adenovirus vectors in which the E1 gene essential for adenovirus growth is deleted. These vectors are known, however, to express adenovirus proteins when they are administered to human and animal individuals, and therefore, from the safety viewpoint, vectors having a structure that rarely causes the expression of virus-coded proteins are desired.

The structure of those vectors is such that foreign genes such as the gene of interest like therapeutic genes have been inserted thereinto and part or all of the genes encoding adenovirus-derived proteins have been deleted therefrom. However, since a virus (vector virus of interest) having such a property cannot propagate by itself, methods have been used in which host cells are co-infected with the virus and another adenovirus (helper virus) and then proteins essential for the adenovirus growth supplied by the helper virus are used to propagate the vector virus of interest together with the helper virus (Mitani, K. et al., Proc. Natl. Acad. Sci..92: 3854–3858 (1995)). In the preparation of recombinant adenoviruses using such helper virus, it is preferred that the amount of the helper virus relative to the vector virus of interest is low, i.e., the growth of the helper virus is suppressed.

As a strategy to that end, a contrivance has been made (Parks, Rj. et al., Proc. Natl. Acad. Sci. 93:13565–13570 (1996)) to suppress the growth of the helper virus wherein a helper virus in which a loxP sequence, a recognition sequence of recombinase Cre, was inserted to the both ends of the packaging signal of the helper virus genome is infected to a host cell that expresses recombinase Cre together with the vector virus of interest so as to remove the packaging signal, with a result that the genomic DNA of the helper virus is no longer packaged into the virus particles.

When a helper virus having inserted a loxP sequence on both sides of the packaging signal thereof is allowed to propagate alone, it is important that the growth is not suppressed and the inserted loxP sequence does not be deleted. In particular, the position of the insertion site of the loxP sequence of the left-hand side of the packaging signal, i.e., the position in between the left inverted terminal repeat (ITR) and the packaging signal is important. It is because the region between the left ITR and the packaging signal in which a foreign gene can be inserted is only 100 bases at most. The insertion site of the loxP sequence of the above-mentioned helper virus is position 188 of the nucleotide sequence of adenovirus type 5 (SEQ ID NO: 9) (Parks, R. J. et al., Proc. Natl. Acad. Sci. 93:13565–13570 (1996)). As another insertion example of the loxP sequence, a site in between the position 193 and 194 of the nucleotide sequence of adenovirus type 5 is reported (SEQ ID NO: 9) (Hardy, S., et at., J. Virol. 71:1842–1849 (1997)). However, all of these insertion sites are immediately before the packaging signal, and it is not known whether these sites are the most suitable as the insertion site of the recombinase recognition sequence.

DISCLOSURE OF THE INVENTION

It is an object of the present invention to provide recombinant adenoviruses in which a recombinase recognition sequence has been inserted at a new site in between the left ITR of the adenovirus and the packaging signal as a material for constructing highly safe vectors for gene therapy in the field of gene therapy.

The present inventors have searched a site into which a recombinase recognition sequence can be inserted in between the left ITR and the packaging signal using human adenovirus type 5, and thereby have found a new insertion site for the recombinase recognition sequence. Based on such finding, we constructed a new recombinant adenovirus in which the loxP sequence, one of the recombinase recognition sequences, has been inserted at said site, and have succeeded in allowing said virus to retain the viral titer equivalent to that of other recombinant viruses in which the loxP sequence has not been inserted at said site.

Thus, the gist of the present invention is a recombinant adenovirus comprising the following sequences in the genome:

(1) a left inverted terminal repeat:

(2) a packaging signal:

(3) a recombinase recognition sequence located at a region in between said left inverted terminal repeat and said packaging signal: and (4) at least one more recombinase recognition sequence which is located downstream of said packaging signal and which is recognized by the recombinase that recognizes the above recombinase recognition sequence.

BRIEF EXPLANATION OF THE DRAWINGS

FIG. 2 shows the nucleotide sequence from positions 1 to 455 of human adenovirus type 5 (SEQ ID NO: 9) and the nucleotide sequence of a synthetic DNA (66 bp (upper strand) and 68 bp (lower strand); SEQ ID NO: 3 and SEQ ID NO: 7, respectively) that contains the loxP sequence inserted in between the ITR and the packaging signal. In the figure, upright and inverted triangles represent the insertion site of a DNA containing the loxP sequence, and the underlined bases represent recognition sequences of restriction enzymes. The nucleotide sequence in bold letters in the inserted DNA represents the 34-base loxP sequence, and the nucleotide sequences in small letters represent recognition sequences of restriction enzymes.

FIG. 3 is a schematic diagram showing the structure of a plasmid pULEFLacZM. In the figure, EF represents EF1α promoter, LacZ represents the E. coli LacZ gene, pA represents the poly(A) sequence, a shaded region represents the loxP sequence, and the dark region represents a mutant loxP sequence. $Ap^R$ represents an ampicillin resistant gene, and ori represents the origin of replication of plasmid.

BEST MODE FOR CARRYING OUT THE INVENTION

Figure 1:
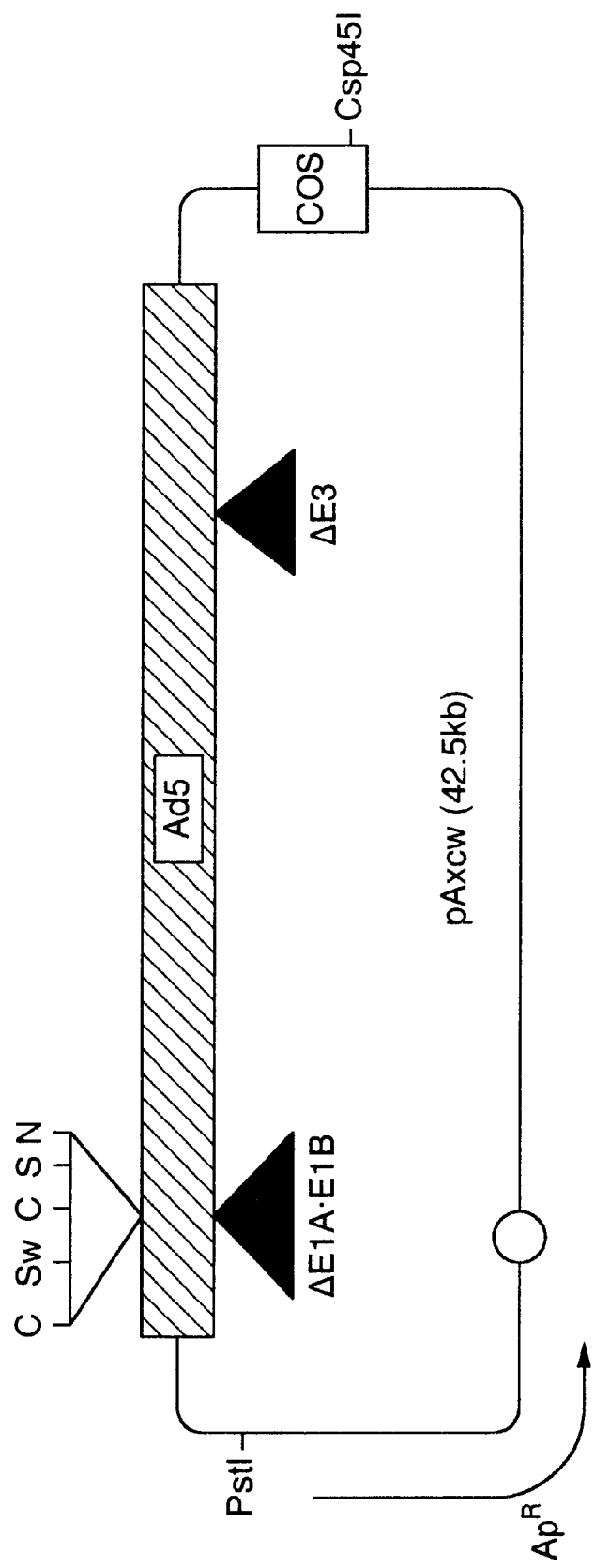
FIG. 1 is a schematic diagram showing the structure of a cosmid vector pAxcw. In the figure, the shaded region represents the adenovirus genome, and C, Sw, S, and N represents restriction enzyme ClaI, SwaI, SalI, and NruI sites, respectively. $Ap^R$ represents an ampicillin resistant gene, and a circle represents the origin of replication of the plasmid.

As used herein the term "recombinant adenovirus" means adenovirus that contains, in the genome thereof, nucleotide sequences other than the nucleotide sequences inherent in adenovirus. The nucleotide sequences other than the nucleotide sequences inherent in adenovirus include, but not limited to, genes encoding proteins, regulatory genes such as promoters and poly(A) sequences, or nucleotide sequences that have no effect on the function.

As used herein the term "left inverted terminal repeat" (hereinafter referred to as left ITR) means a nucleotide sequence present on the left end (that is, upstream of the E1 gene) among the nucleotide sequences on both ends of the genome essential for the initiation of replication of adenovirus genome. Specific examples thereof include a nucleotide sequence at positions 1 to 103 in human adenovirus type 5 (SEQ ID NO: 9).

As used herein the term "packaging signal" means a nucleotide sequence essential for an adenovirus genomic DNA to be inserted into adenovirus particles. Specific examples thereof include a nucleotide sequence at positions 195 to 358 in human adenovirus type 5 SEQ ID NO: 9).

As used herein the term "recombinase recognition sequence" means a nucleotide sequence recognized by a specific DNA recombination enzyme "recombinase", and a nucleotide sequence that permits the entire process of cleavage, exchange, and binding of DNA strands in between two "recombinase recognition sequences" in the presence of "recombinase."

Examples of "recombinase" include Cre, a recombinase derived from bacteriophage P1 (Sternberg et al., J. Mol. Biol. 150:467–486 (1981)), FLP (Babineau et al., J. Biol. Chem. 260:12313–12319 (1985)) encoded by 2 micron DNA of yeast (*Saccharomyces cereviceae*), R derived from the pSR1 plasmid of *Zygosaccharomyces rouxii* (Matsuzaki et al., Mol. Cell. Biol. 8:955–962 (1988)), and the like.

As used herein the term "downstream region of the packaging signal" means a region in between the packaging signal and the right (that is, downstream of the E1 gene) ITR. Specific examples include a nucleotide sequence at positions 359 and after in human adenovirus type 5 (SEQ ID NO: 9).

As used herein the term "a recombinase recognition sequence becomes a substrate for recombinase Cre derived from bacteriophage P1" means that recombinase Cre causes the entire process of cleavage, exchange, and binding of DNA strands in between two "recombinase recognition sequences." As typical examples of "recombinase recognition sequences," there can be mentioned the loxP sequence (Abremski et al., J. Biol. Chem. 1509–1514 (1984) and Hoess et al., Proc. Natl. Acad. Sci. 81:1026–1029 (1984)) comprising 34 bases in bacteriophage P1. The loxP sequence is a DNA sequence comprising the following nucleotide sequence (hereinafter this sequence is referred to as the wild type loxP sequence):

5'-ATAACTTCGTATA ATGTATGC TATACGAAGTTAT-3' (SEQ ID NO: 1)
3'-TATTGAAGCATAT TACATACG ATATGCTTCAATA-5' (SEQ ID NO: 2)
(in the above sequence, the underlined portion represents a spacer region)

As used herein the term "'a recombinase recognition sequence' that becomes a substrate for recombinase Cre" need not be limited to the above wild type loxP sequence, and part of the wild type loxP sequence may be replaced with other bases as long as the two "recombinase recognition sequences" become substrates for recombinase Cre. Furthermore, even those loxP sequences (mutant loxP sequences) that normally do not become substrates for recombinase Cre in a combination with the wild type loxP sequence but become substrates for recombinase Cre in a combination with the mutant loxP sequences of the same sequence by base replacement of the wild type loxP sequence, i.e., sequences for which the entire process of cleavage, exchange, and binding of DNA strands takes place, are included in the recognition sequences of recombinase Cre. As an example of such mutant loxP sequences, there can be mentioned a loxP sequence (Hoess et al., Nucleic Acids Res. 14:2287–2300 (1986)) in which one base in a spacer region of the wild type loxP sequence has been replaced and loxP sequences (Lee, G. et al., Gene 14:55–65 (1998)) in which two bases in the spacer region have been replaced.

As used herein the term "a recombinase recognition sequence becomes a substrate for recombinase FLP" means that recombinase FLP causes the entire process of cleavage, exchange, and binding of DNA chains in between two "recombinase recognition sequences." As typical examples of "recombinase recognition sequences," there can be mentioned a yeast-derived FRT sequence (Babineau et al., J. Biol. Chem. 260:12313–12319 (1985)). The FRT sequence is a 34-base DNA sequence, and the original sequence (wild type FRT sequence) has been defined to have only one meaning in the same way as for the wild type loxP sequence. In accordance with the present invention, however, "'a recombinase recognition sequence" that becomes a substrate for recombinase FLP" is not necessarily be limited to the above wild type FRT sequence, and part of the wild type FRT sequence may be replaced with other bases as long as two "recombinase recognition sequences" can become substrates for recombinase FLP. Furthermore, even those FRT sequences (mutant FRT sequences) that normally do not become substrates for recombinase FLP in a combination with the wild type FRT sequence but become substrates for recombinase in a combination with the mutant FRT sequences of the same sequence by base replacement of the wild type FRT sequence, i.e., sequences for which the entire process of cleavage, exchange, and binding of DNA strands takes place, are included in the recognition sequences of recombinase FLP.

The recombinant adenovirus of the present invention may further contain a foreign gene, and examples of such foreign genes include therapeutic genes for humans, so-called reporter genes such as the LacZ gene and recombinase, and the like. As an insertion site for foreign genes, there can be mentioned the E1 gene deleted site, the E3 gene deleted site, and the like.

Sources of the recombinant adenovirus for use in the present invention are preferably, but not limited to, human-derived adenoviruses. In human-derived adenoviruses, type 2 or type 5 that is classified into type C is preferred. The present invention will be explained in further details with reference to human adenovirus type 5 and the loxP sequence (wild type) as an example of "recombinase recognition sequence" hereinbelow.

As a method of constructing recombinant adenovirus, there are known a method of directly ligating the DNA of interest to adenovirus genomic DNA, a method in which the DNA of interest is inserted to one of the two plasmids to which a divided adenovirus genome was inserted, and then subjected to homologous recombination to construct a recombinant adenovirus, and other methods. In accordance with the present invention, however, it is preferred to construct a recombinant adenovirus by a method in which the gene of interest is inserted to a cosmid vector containing most of the adenovirus genome, and then the cosmid vector and a restriction enzyme-digested adenovirus DNA-terminal protein complex are subjected to homologous recombination (the COS-TPC method: Miyake et al., Proc. Natl. Acad. Sci. 93:1320–1324 (1996), and Japanese Unexamined Patent Publication (Kokai) No. 7-298877) to construct said recombinant adenovirus. It is because such a method yields the desired recombinant adenovirus at a very high efficiency.

Firstly, a cosmid vector pAxcw15L is constructed in which a loxP sequence has been inserted in between at positions 147 and 148 of the nucleotide sequence located in between the left ITR and the packaging signal of a cosmid vector pAxcw (FIG. 1, Japanese Unexamined Patent Publication (Kokai) No. 8-308585, pAdexlcw and pAxcw are identical) containing most of the genome of adenovirus type 5 other than the adenovirus E1 and E3 genes. At this time, DNA containing the adenovirus genome is cleaved with a restriction enzyme AflIII in which a recognition sequence is present at positions 143–148 of the nucleotide sequence, and then, after blunt-ending by treatment with the Klenow enzyme, a 65-base synthetic DNA containing the loxP sequence is ligated. This procedure produces four overlapping bases at the loxP insertion site that are overhung due to AflIII digestion. Thus, the insertion in which positions 147 and 148 of the nucleotide sequence means the insertion of the loxP sequence at any position in between positions 143–148 of SEQ ID NO: 9.

In order to compare with a conventionally known insertion site (position 188 or 193 of the nucleotide sequence (SEQ ID NO: 9)), a cosmid vector pAxcw19L is constructed in which a loxP sequence is inserted in between positions 191 and 192 located in the above insertion site. In this case also, DNA containing the adenovirus genome is cleaved with a restriction enzyme AgrAI in which a recognition sequence is present at positions 186–193 of the nucleotide sequence, and then, after blunt-ending by treatment with the Klenow enzyme, a 65-base synthetic DNA containing the loxP sequence is ligated, with a result that four overlapping bases at the loxP insertion site are present that are overhung due to SgrAI digestion. Thus, the insertion in which positions 191 and 192 of the nucleotide sequence means the insertion of the loxP sequence at any position in between positions 187–192 of SEQ ID NO: 9.

Figure 4:
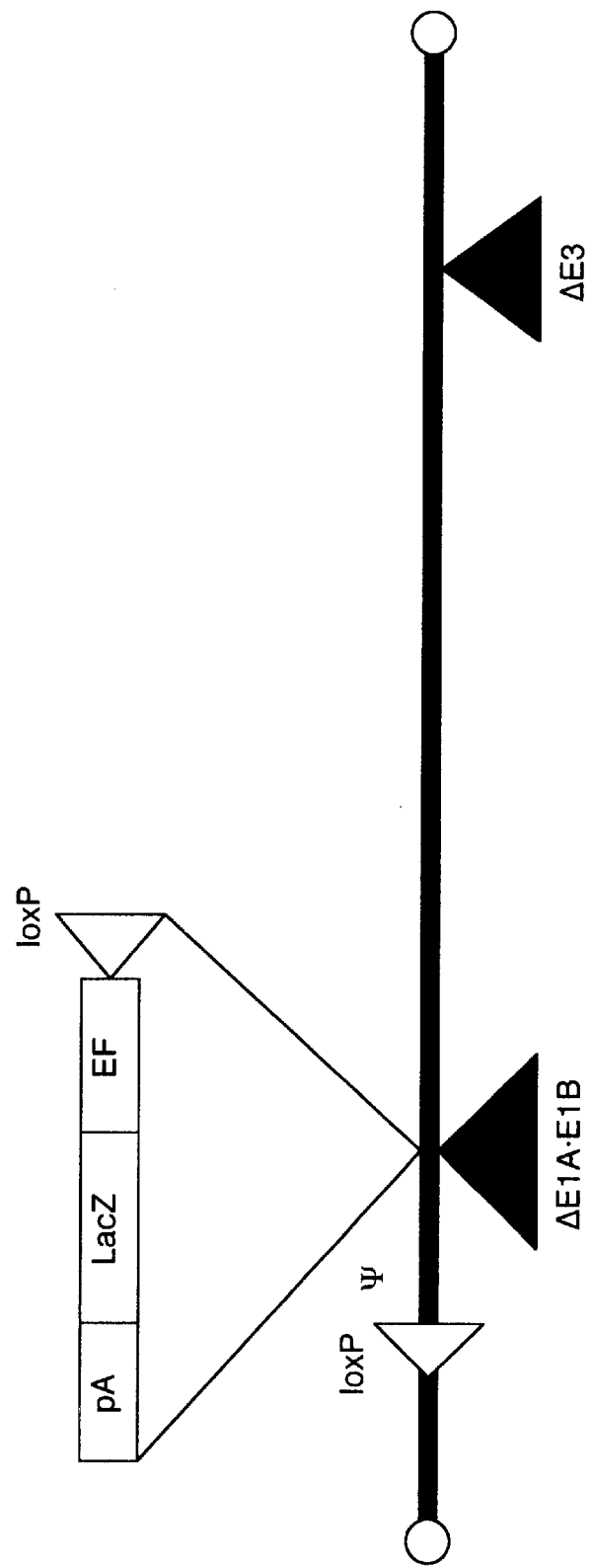
FIG. 4 is a schematic diagram of the structure of recombinant adenoviruses (AxLEFLacZ15L and AxLEFLacZ19L). In the figure, the thick line represents the adenovirus genome, the dark triangle represents a deleted adenovirus gene, the open triangle represents the loxP sequence, EF represents the EFlα promoter, LacZ represents the *E. coli* LacZ gene, pA represents the poly(A) sequence, and ψ represents the adenovirus packaging signal.

Then a cosmid vector pAxLEFLacZ15L is constructed in which a loxP sequence/EF1α promoter/LacZ/poly(A) sequence has been inserted at the E1 gene deleted site of the cosmid vector pAxcw15L. Similarly a cosmid vector pAxLEFLacZ19L is constructed in which a loxP sequence/EF1α promoter/LacZ/poly(A) sequence has been inserted to the cosmid vector pAxcw19L. These cosmid vectors are used to construct the desired recombinant adenoviruses AxLEFLacZ15L and AxLEFLacZ19L (FIG. 4) by the above-mentioned COS-TPC method. The COS-TPC method developed by the present inventors yields the desired recombinant adenovirus at a very high efficiency, in which after the cells transformed with the restriction enzyme-digested adenovirus DNA-terminal protein complex and a cosmid vector having the structure of the virus of interest, more than half of any clones selected are the desired recombinant virus (Miyake et al., Proc. Natl. Acad. Sci. 93:1320–1324 (1996)).

The frequency at which the desired clone appears during the construction of the recombinant adenovirus AxLEFLacZ15L is for example 4 out of 6 clones, which is almost the same as that of the desired clone commonly obtained during recombinant adenovirus construction by the present inventors. On the other hand, the frequency at which the desired clone appears during the construction of the recombinant adenovirus AxLEFLacZ19L is for example 3 out of 12 clones, which is evidently low. Furthermore, AxLEFLacZ15L retains almost the same titer as the common recombinant adenovirus. The difference in the appearance frequency of the desired recombinant adenoviruses reflects the effect the loxP sequence inserted in between the ITR and the packaging signal has on the growth of adenovirus. Thus, it was found that the insertion at positions 143–148 of the nucleotide sequence (SEQ ID NO: 9) (AxLEFLacZ15L) has little effect on adenovirus growth, the insertion at positions 187–192 of the nucleotide sequence (SEQ ID NO: 9) has a negative effect on the growth cycle of the virus including the process of packaging into viral particles of adenovirus DNA. Therefore, the insertion site at positions 143–148 of the nucleotide sequence (SEQ ID NO: 9) newly discovered by the present inventors is more suitable for the growth of adenovirus than the conventionally known insertion site (at position 188 or 193 of the nucleotide sequence (SEQ ID NO: 9)).

The recombinant adenovirus thus obtained in which the loxP sequence has been inserted at positions 143–148 of the nucleotide sequence (SEQ ID NO: 9) can be allowed to act as a helper virus by inserting another loxP at any position on the rightward to the packaging signal. The method as mentioned above comprises infecting a helper virus in which a loxP sequence, a recombinase Cre recognition sequence, has been inserted at both sides of the packaging signal of the helper virus genome to a host cell that expresses recombinase Cre together with the desired vector virus, and then removing the packaging signal thereby rendering the genomic DNA of the helper virus incapable of being packaged into virus particles, so that the growth of the helper virus is suppressed (Parks, R. J. et al., Proc. Natl. Acad. Sci. 93:13565–13570 (1996)). The insertion site for another loxP sequence on the rightward to the packaging signal include, but not limited to, a deletion site of the adenovirus E1A gene. The adenovirus AxLEFLacZ15L of the present invention is one such example.

Figure 5:
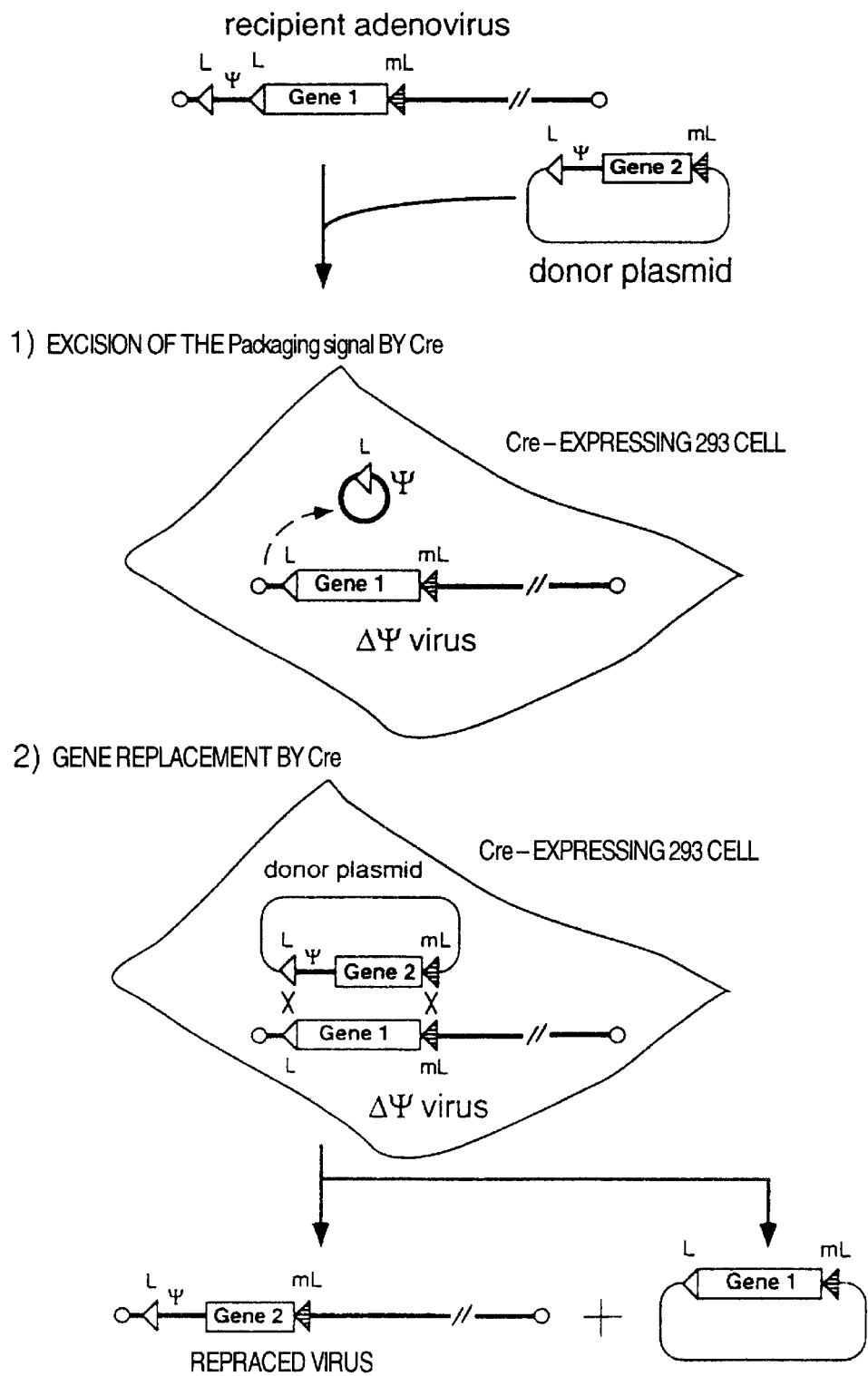
FIG. 5 is a schematic diagram showing a method of constructing gene-replacement typed recombinant adenovirus. In the figure, L represents a wild type loxP sequence. mL represents a mutant loxP sequence, ψ represents the adenovirus packaging signal, the thick line represents an adenovirus genome, and the open circle represents the adenovirus terminal protein.

Furthermore, by combining with the mutant loxP sequence mentioned above, the recombinant adenovirus of the present invention can be used for construction of a gene-replaced recombinant adenovirus. As used herein the term "construction of a gene-replaced recombinant adenovirus" means a method in which the gene 1 of a recombinant adenovirus having a foreign gene 1 is replaced with gene 2 present in other DNA molecules such as plasmid in the presence of recombinase Cre. One example of such a method is explained below (FIG. 5).

For a gene-replacement recombinant adenovirus having gene 1, a recombinant adenovirus in which the wild type loxP sequence and the mutant loxP sequence are inserted in the order of the left ITR/wild type loxP sequence (inserted at positions 143–148 of the nucleotide sequence (SEQ ID NO: 9))/gene 1/mutant loxP sequence is constructed. A fragment of the wild type loxP sequence/gene 1 is inserted into the E1 deleted site. As a plasmid having gene 2, there can be mentioned a plasmid having the structure of a wild type loxP sequence (inserted at positions 143–148 of the nucleotide sequence (SEQ ID NO: 9))/packaging signal/ gene 2/mutant loxP sequence. When a recombinant adenovirus having gene 1 and a plasmid having gene 2 are introduced concurrently or sequentially into Cre protein-expressing cells such as Cre expressing 293 cells, the packaging signal flanked by the two wild type loxP sequences is eliminated in recombinant adenovirus for gene transfer, and a recombinant adenovirus is generated in which the wild type loxP sequence/gene 1/mutant loxP sequence has been replaced with the wild type loxP sequence/ packaging signal/gene 2/mutant loxP sequence derived from plasmid. In the recombinant adenovirus for gene transfer that was not subjected to gene replacement, the packaging signal flanked by the two wild type loxP sequences is eliminated so that though the viral DNA replicates, it is not packaged into infectious particles and cannot propagate as virus. On the other hand, since the gene-replaced adenovirus has the packaging signal introduced from the plasmid, it is packaged into the infectious particles and thereby propagate, so that recombinant adenoviruses in which "gene 1" has been replaced with "gene 2" are obtained at a high frequency.

Furthermore, by changing the insertion position of the mutant loxP sequence of the recombinant adenovirus for gene transfer, a recombinant adenovirus in which part or all of the gene encoding adenovirus-derived protein has been eliminated can be constructed. As an example of the insertion position of the mutant loxP sequence herein, there can be mentioned an untranslated region in between the adenovirus L3 gene and the E2A gene, the E3 gene-deleted site, a region in between the upstream region of the E4 gene and the right ITR, and the like. When a mutant loxP sequence is inserted into these positions for gene replacement, it is necessary to control the size of the DNA in between the wild type loxP sequence-mutant loxP sequence of the plasmid having gene B so as to attain efficient packaging of the generated adenovirus DNA into infectious particles. In the generated recombinant adenovirus, not only "gene A" is replaced with "gene B," but DNA in the wild type loxP sequence/gene A/mutant loxP sequence is replaced with DNA in the wild type loxP sequence-(gene B)-mutant loxP sequence of the plasmid, it is possible to construct a recombinant adenovirus in which the adenovirus gene otherwise present in between the gene A/mutant loxP sequence is removed.

The present invention will now be explained in more details with reference to the following Examples. It should be noted, however, that the present invention is not limited by these Examples in any way and that modifications known in the field of art of the present invention may be made. Unless otherwise noted, various procedures in handling phage, plasmid, DNA, various enzymes, Escherichia coli, cultured cells, and the like were performed in accordance with the method as described in "Molecular Cloning, A Laboratory Manual, edited by T. Maniatis, et al., The Second edition (1989), Cold Spring Harbor Laboratory."

EXAMPLE 1

Construction of a cosmid vector for construction of a recombinant adenovirus in which the loxP sequence has been inserted in between positions 147 and 148 of the nucleotide sequence of adenovirus type 5 genome (SEQ ID NO: 9)

1) A cosmid vector pAxcw (FIG. 1, Japanese Unexamined Patent Publication (Kokai) No. 8-308585, page 15, pAdex-lcw is identical with pAxcw) which contains most of the adenovirus type 5 genome other than adenovirus E1 and E3 genes and in which a polylinker has only been inserted into the E1 gene-deleted site was digested with SalI, and then was subjected to self-ligation, thereby to obtain plasmid pxcw (3.1 kb) containing about 0.4 kb of the left end of the adenovirus genome.

The plasmid pxcw was then digested with AflIII, was blunt-ended on both ends with the Klenow enzyme, to which was ligated a 66-base synthetic DNA (nucleotide sequence: 5'-GCTCGAGATAACTTCGTATAATGTATGCTATACG AAGTTATACGCGTTCGCTCGGTACCCGCCATG-3' (SEQ ID NO: 3) containing the loxP sequence and its complementary strand, see FIG. 2) to obtain a plasmid pycw15L (3.2 kb) in which the loxP sequence has been inserted in between positions 147 and 148 of the adenovirus genome (SEQ ID NO: 9). The nucleotide sequence from the left end to 521 bp of the adenovirus type 5 genome in the plasmid pycw15L is shown in FIG. 2 and SEQ ID NO: 4.

2) The cosmid vector pAxcw was simultaneously digested with SwaI and Csp45I to obtain an about 28 kb fragment (a) containing most of the adenovirus genome. The cosmid vector pAxcw was also simultaneously digested with Csp45I and PstI to obtain an about 13 kb fragment (b) not containing the adenovirus genome. Furthermore, the plasmid pycw15L was simultaneously digested with SwaI and PstI to obtain an about 1.2 kb fragment (c) containing the left end of the adenovirus genome. Then, the three fragments (a), (b), and (c) were ligated to obtain a cosmid vector pAxcw15L which contains most of the adenovirus genome and in which the loxP sequence has been inserted in between positions 147 and 148 (SEQ ID NO: 9).

3) The plasmid puLwL (Lee G. et al., Gene 14:55–65 (1998)) in which the wild type loxP sequence/restriction enzyme SwaI site/wild type loxP sequence has been inserted at a restriction enzyme Ec1136II site of the plasmid pUC119 was digested with a restriction enzyme XhoI, and then a 60-base synthetic DNA (SEQ ID NO: 5 and SEQ ID NO: 6) containing a mutant loxP sequence and a restriction enzyme NheI site was ligated thereto to obtain a plasmid puLwM in which the wild type loxP sequence present in between the SwaI site and the ampicillin resistant gene has been replaced to a mutant loxP sequence.
5'-TCGAGTCCGGAATAACTTCGTATAACGTATACT ATACGAAGTTATGCTAGCATTTAAATG-3' (SEQ ID NO: 5)
3'-CAGGCCTTATTGAAGCATATTGCATATGATATG CTTCAATACGATCGTAAATTTACAGCT-5' (SEQ ID NO: 6)

4) After a plasmid pEFLacZ (Japanese Unexamined Patent Publication (Kokai) No. 7-298877, page 11) that expresses the LacZ gene under the control of the EF1α promoter was digested with HindIII, it was blunt-ended to obtain a fragment containing the promoter/LacZ/poly(A) sequence. This fragment was inserted into the SwaI site of the plasmid pULwM obtained in the above 3) in which the loxP sequence/SwaI site/mutant loxP sequence was inserted at the Ec1136II site of plasmid pUC119 to obtain a plasmid pULEFLacZM (9.1 kb, FIG. 3). Then, the plasmid pULE-FLacZM was simultaneously digested with NheI and Asp718 and then blunt-ended to obtain a fragment containing the loxP sequence/promoter/LacZ/poly(A) sequence. Furthermore, this fragment was inserted into the SwaI site of the cosmid pAxcw15L to obtain a cosmid pAxLEFLacZ15L.

EXAMPLE 2

Construction of a cosmid vector for construction of a recombinant adenovirus in which the loxP sequence has been inserted in between positions 191 and 192 of the nucleotide sequence of adenovirus type 5 genome (SEQ ID NO: 9)

1) After the plasmid pxcw constructed in 1) of Example 1 was digested with SgrAI, the both ends of them were blunt-ended with the Klenow enzyme, and then a 68-base synthetic DNA (nucleotide sequence: 5'-GTACTCGAGATAACTTCGTATAATGTATGCTATA CGAAGTTATACGCGTTCGCTCGGTACCCGGCCGG-3' (SEQ ID NO: 7) and its complementary strand, see FIG. 2) was inserted to obtain a plasmid pycw19L (3.2 kb) in which the loxP sequence was inserted in between positions 191 and 192 of the adenovirus genome (SEQ ID NO: 9). The nucleotide sequence from the left end to 523 bp of the adenovirus type 5 genome in the plasmid pycwl9L is shown in FIG. 2 and SEQ ID NO: 8.

2) The three fragments of an about 1.2 kb fragment containing the left end of the adenovirus genome obtained by simultaneously digesting the plasmid pycw19L with SwaI and PstI, a fragment (a) obtained by simultaneously digesting pAxcw with SwaI and Csp45I prepared in 2) of Example 1 and a fragment (b) obtained by simultaneously digesting pAxcw with Csp45I and PstI were ligated to obtain a cosmid vector pAxcw19L which contains most of the adenovirus genome and in which the loxP sequence has been inserted in between positions 191 and 192 (SEQ ID NO: 9).

3) A fragment containing the loxP sequence/promoter/LacZ/]poly(A) sequence prepared in 4) of Example 1, obtained from the plasmid pULEFLacZM was inserted into the SwaI site of the cosmid pAxcw19L to obtain a cosmid pAxLEFLacZ19L.

EXAMPLE 3

Construction of a recombinant adenovirus in which the loxP sequence has been inserted in between positions 147 and 148 or in between positions 191 and 192 of the nucleotide sequence of adenovirus type 5 genome (SEO ID NO: 9) and which has the expression unit of the LacZ gene 1) Construction of a recombinant adenovirus Using the cosmid vectors (pAxLEFLacZ15L, pAxLEFLacZ19L) constructed in Examples 1 and 2, a recombinant adenovirus was constructed in which the loxp sequence was inserted in between the ITR of a replication-deficient adenovirus vector (the E1 and E3 genes are deleted) derived from adenovirus type 5 and the packaging signal, and in which the loxp sequence/EF1α promoter/LacZ/poly(A) sequence has been inserted into the E1 gene-deleted site. The methods of constructing recombinant adenovirus and of identifying he desired recombinant adenovirus by restriction enzyme digestion of viral DNA were performed in accordance with the known method (Miyake et al., Proc. Natl. Acad. Sci. 93:1320–1324 (1996), and Japanese Unexamined Patent Publication (Kokai) No. 7-298877).

The viral DNA-terminal protein complex of Ad5-dlX (Saito, I. et al., J. Virol. 54:711–719 (1985)) in which the E3 gene is deleted, derived from human adenovirus type 5 was digested with a restriction enzyme EcoT22I. 293 cells cultured in a 6 cm dish were transfected with this viral DNA-terminal protein complex and a cosmid vector pAxLEFLacZ15L (constructed in Example 1) or a cosmid vector pAxLEFLacZ19L (constructed in Example 2) by the calcium phosphate coprecipitation method. On the following day, the transformed cells were diluted and then plated again on a 96-well microplate and cultured for 2–3 weeks. Some of the wells in which cytopathic effect was observed due to viral propagation were selected to prepare viral solutions (1st seed viral stocks), and 2 wells each of 293 cells cultured in a 24-well microplate were infected with this viral solution. After cytopathic effect occurred, viral DNA was prepared from one of the two wells using a known method. After digesting the viral DNA with XhoI, the genome structure of the virus was analyzed by electrophoresis to identify the recombinant adenovirus (AxLEFLacZ15L or AxLEFLacZ19L, FIG. 4) clone of interest.

Normally, for the recombinant adenovirus thus constructed, more than half of the arbitrarily selected viral clones are viral clones of interest. In the case of AxLEFLacZ15L, 4 out of 6 clones are the clone of interest, and the appearance frequency is almost the same as that of the clones of interest normally observed in construction of recombinant adenovirus by the present inventors. On the other hand, in the case of AxLEFLacZ19L, 3 out of 12 clones were the clones of interest, and the appearance frequency was lower than that of AxLEFLacZ15L.

From wells that were not used for the analysis of viral DNA, the viral solutions (2nd seed viral stocks) of #3 clones of AxLEFLacZ15L and #3 clones of AxLEFLacZ19L were prepared, which were further scaled up to passage virus, and finally the 4th seed viral stocks were obtained.

2) Titration of AxLEFLacZ15L and AxLEFLacZ19L

The titers of the 4th seed viral stocks of AxLEFLacZ15L and AxLEFLacZ19L were determined using 293 cells. Titration was performed by the limiting dilution method using a 96-well microplate in accordance with a known method (Japanese Unexamined Patent Publication (Kokai) No. 7-298877).

As a result, the titer of AxLEFLacZ15L was $3.4 \times 10^8$ PUF/ml, and that of AxLEFLacZ19L was $3.4 \times 10^8$ PFU/ml, indicating that the titers of both viruses were the almost same titers as the normal replication-deficient recombinant adenovirus. Thus, the insertion of the foreign gene containing loxP sequence in between the ITR and the packaging signal was found not to inflict a lethal damage to the growth of adenovirus.

INDUSTRIAL APPLICABILITY

The present invention provides recombinant adenovirus that becomes a material for constructing highly safe vectors for gene therapy in the field of gene therapy. The present invention permits efficient production of recombinant adenovirus vectors in which genes essential for the growth of adenovirus are deleted, and the production of gene-replaced recombinant adenovirus vectors, and which facilitates the supply of recombinant adenovirus that can be used in the field of gene therapy.

What is claimed is:

1. A recombinant adenovirus comprising the following sequences in the genome:
   (1) a left inverted terminal repeat:
   (2) a recombinase recognition sequence located at any site from nucleotides 143 to 148 of the nucleotide sequence of human adenovirus type 5 (SEQ ID NO: 9) wherein the location of the recombinase recognition sequence at the site has little effect on the growth adenovirus:
   (3) a packaging signal: and
   (4) at least one more recombinase recognition sequence which is located between said packaging signal and a right inverted terminal repeat and which is recognized by the recombinase that recognizes the above recombinase recognition sequence, wherein the genomic portions of the adenovirus are derived from human adenovirus type 5.

2. The recombinant adenovirus according to claim 1 wherein the recombinase recognition sequence is a substrate for recombinase Cre derived from bacteriophage P1.

3. The recombinant adenovirus according to claim 2 wherein the recombinase recognition sequence is the loxP sequence.

4. The recombinant adenovirus according to claim 1 wherein the recombinase recognition sequence is a substrate for recombinase FLP derived from yeast.

5. The recombinant adenovirus according to claim 4 wherein the recombinase recognition sequence is a FRT sequence.

* * * * *